United States Patent [19]

George et al.

[11] Patent Number: 4,990,506

[45] Date of Patent: Feb. 5, 1991

[54] 3-(ACYLAMINOMETHYL)IMIDAZO(1,2-A)PYRIDINE DERIVATIVES AND THEIR APPLICATION IN THERAPY

[75] Inventors: Pascal George, Vitry Sur Seine; Claudie Giron, Antony; Jacques Froissant, Moree, all of Belgium

[73] Assignee: Synthelabo, Paris, France

[21] Appl. No.: 425,870

[22] Filed: Oct. 24, 1989

Related U.S. Application Data

[60] Division of Ser. No. 204,748, Jun. 10, 1988, Pat. No. 4,891,371, which is a continuation of Ser. No. 10,703, Feb. 4, 1987, Pat. No. 4,767,755.

[51] Int. Cl.$^5$ .................. C07D 471/04; A61K 31/44
[52] U.S. Cl. .................. 514/212; 514/228.2; 514/233.2; 514/253; 514/300; 540/524; 544/58.6; 544/127; 544/326; 546/121
[58] Field of Search .............. 546/121; 540/524; 544/58.6, 127, 326; 514/300, 212, 228.2, 233.2, 253

[56] References Cited

U.S. PATENT DOCUMENTS 4,650,796 3/1987 George et al. .................. 546/121

Primary Examiner—Mary C. Lee
Assistant Examiner—Bernard I. Dentz
Attorney, Agent, or Firm—Wegner, Cantor, Mueller & Player

[57] ABSTRACT

A compound which is a 3-(acylaminomethyl)imidazo[1,2-a]pyridine derivative of formula (I)

in which
$R_1$ denotes hydrogen; linear or branched $C_1$-$C_4$ alkyl; or benzyl;
$R_2$ denotes linear or branched $C_1$-$C_6$ alkyl; cyclohexyl; trichloromethyl; 1-propenyl; allyl; phenyl; 4-chlorophenyl; or benzyl:
or $R_1$ and $R_2$ together denote a $C_3$-$C_5$ aliphatic chain:
X denotes halogen; $C_1$-$C_3$ alkyl; methylthio; trifluoromethyl; optionally esterified carboxy of formula —COOR in which R denotes hydrogen or $C_1$-$C_6$ alkyl; cyano; optionally mono- or dialkylated aminocarbonyl of formula —CONR$_3$R$_4$ in which $R_3$ and $R_4$ independently denote hydrogen or $C_1$-$C_4$ alkyl or together denote a chain of formula —(CH$_2$)$_2$—Z—(CH$_2$)$_2$— in which Z denotes a direct bond, oxygen, sulphur, or a divalent group of formula —CH$_2$—, —NH— or —N($C_1$-$C_4$ alkyl)—; alkylamino of formula NHR$_5$ in which $R_5$ denotes $C_2$-$C_6$ alkyl; or dialkylamino of formula —NR$_6$R$_7$ in which $R_6$ and $R_7$ independently denote $C_2$-$C_6$ alkyl or together denote a chain of formula —(CH$_2$)$_2$—Z—(CH$_2$)$_2$— in which Z denotes a direct bond, oxygen, sulphur, or a divalent group of formula —CH$_2$—, —NH— or —N($C_1$-$C_4$ alkyl)—: and Y denotes hydrogen; halogen; methyl; trifluoromethyl; optionally esterified carboxy of formula —COOR$_8$ in which $R_8$ denotes hydrogen or $C_1$-$C_6$ alkyl; cyano; optionally mono- or dialkylated aminocarbonyl of formula —CONR$_9$R$_{10}$ in which $R_9$ and $R_{10}$ independently hydrogen or $C_1$-$C_4$ alkyl; or optionally mono- or dialkylated amino of formula —NR$_{11}$R$_{12}$ in which $R_{11}$ and $R_{12}$ independently denote hydrogen or $C_1$-$C_4$ alkyl: with the exclusion of compounds in which X denotes halogen; alkyl; or methylthio and Y denotes hydrogen; halogen; or methyl:
or a pharmacologically acceptable acid addition salt is useful in therapy.

2 Claims, No Drawings

3-(ACYLAMINOMETHYL)IMIDAZO(1,2-A)PYRIDINE DERIVATIVES AND THEIR APPLICATION IN THERAPY

This application is a divisional of U.S. Ser. No. 224,748, filed June 10, 1988, now U.S. Pat. No. 4,891,371 which is a continuation of U.S. Ser. No. 010,723, filed Feb. 4, 1987 now U.S. Pat. No. 4,767,755.

The present invention provides compounds which are 3-(acylaminomethyl)imidazo[1,2-a]pyridine derivatives of formula (I) given in the scheme given below, in which $R_1$ denotes hydrogen; linear or branched $C_1$-$C_4$ alkyl; or benzyl:

$R_2$ denotes linear or branched $C_1$-$C_6$ alkyl; cyclohexyl; trichloromethyl; 1-propenyl; allyl; phenyl; 4-chlorophenyl; or benzyl:

or alternatively $R_1$ and $R_2$ together denote a $C_3$-$C_5$ aliphatic chain:

X denotes halogen; $C_1$-$C_3$ alkyl; methylthio; trifluoromethyl; optionally esterified carboxy group of formula COOR in which R denotes hydrogen or $C_1$-$C_6$ alkyl; cyano; optionally mono-or dialkylated aminocarbonyl of formula $CONR_3R_4$ in which $R_3$ and $R_4$ independently denote hydrogen or $C_1$-$C_4$ alkyl or together denote a chain of formula —(CH$_2$)$_2$—Z—(CH$_2$)$_2$— in which Z denotes a direct bond, oxygen, sulphur or a divalent group of formula —CH$_2$—, —NH— or —N(C$_1$-C$_4$ alkyl)—; alkylamino of formula $NHR_5$ in which $R_5$ denotes $C_2$-$C_6$ alkyl; or a dialkylamino of formula $NR_6R_7$ in which $R_6$ and $R_7$ independently denote $C_2$-$C_6$ alkyl or together denote a chain of formula —(CH$_2$)$_2$—Z—(CH$_2$)$_2$— in which Z denotes a direct bond, oxygen, sulphur or a divalent group of formula —CH$_2$—, —NH— or —N(C$_1$-C$_4$ alkyl)-:
and Y denotes hydrogen; halogen; methyl; trifluoromethyl; optionally esterified carboxy of formula $COOR_8$ in which $R_8$ denotes hydrogen or $C_1$-$C_6$ alkyl; cyano; optionally mono- or dialkylated amino carbonyl of formula $CONR_9R_{10}$ in which $R_9$ and $R_{10}$ independently denote hydrogen or $C_1$-$C_4$ alkyl; or optionally mono- or dialkylated amino of formula $NR_{11}R_{12}$ in which $R_{11}$ and $R_{12}$ independently denote hydrogen or $C_1$-$C_4$ alkyl;
with the exclusion of compounds in which X denotes halogen; alkyl; or methylthio and Y denotes hydrogen; halogen or methyl;
or their pharmacologically acceptable acid addition salts.

The preferred compounds are those in which $R_1$ denotes hydrogen or methyl and $R_2$ denotes propyl or isobutyl.

The compounds of the invention can be prepared according to the scheme on the following page.

A 2-aminopyridine of formula (II), bearing a substituent Y, is reacted with a 2-bromoethanone of formula (III) bearing the substituent X, preferably in a protic solvent such as an aliphatic alcohol and in a heated state and in the absence or presence of a base such as an alkali metal carbonate or hydrogen carbonate. The imidazo[1,2-a]pyridine of formula (IV) thereby obtained is hydroxymethylated, for example by means of formaldehyde in a solvent of the carboxylic acid type, such as acetic acid, or any other equivalent means, to obtain an alcohol of formula (V).

The alcohol of formula (V) can also be obtained from the imidazo[1,2-a]pyridine of formula (IV) in two stages, the first being a formylation, for example by means of a reagent which can be obtained by the action of oxalyl chloride on dimethylformamide. After hydrolysis, an aldehyde is obtained which, in the second stage, is reduced to the corresponding alcohol of formula (V), in a known manner, for example by the action of an alkali metal borohydride.

SCHEME

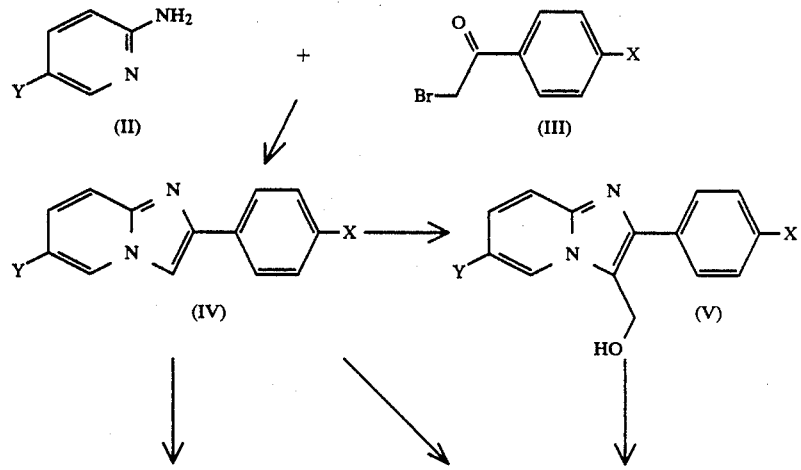

SCHEME

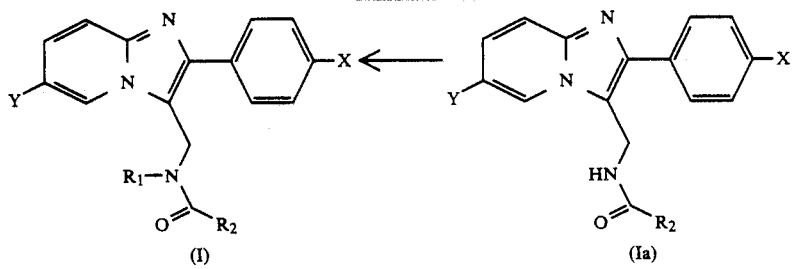

The alcohol (v) is then reacted with a nitrile of formula $R_2$—CN in an acid medium, for example an acetic or sulfuric acid medium, preferably at a temperature of from 0° to 150° C., depending on the nitrile used. After hydrolysis, a compound of formula (Ia), in which the substituent $R_1$ is hydrogen, is obtained. If desired, it is possible to alkylate or benzylate this compound in a known manner, for example with a halide of formula $R_1$-hal in the presence of an alkali metal hydride, and in a suitable solvent such as tetrahydrofuran, to yield a compound of formula (1) in which $R_1$ is an alkyl or benzyl group.

The compounds of formula (I) can also be prepared in two stages by reacting the imidazopyridine of formula (IV) with an amide of formula

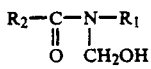

in which $R_1$ and $R_2$ are as defined above. The reaction is generally performed at room temperature, preferably in the presence of concentrated sulphuric acid and optionally with a cosolvent such as glacial acetic acid.

It is also possible to prepare compounds of formula (Ia) by reacting the imidazopyridine of formula (IV) with a nitrile of formula $R_2$—CN and paraformaldehyde, generally in the heated state, preferably in acetic acid medium and in the presence of sulphuric acid.

The compound (Ia) obtained after hydrolysis can then, if so desired, be alkylated or benzylated as described above.

The compounds of formula (1) in which X and/or Y denote an amino group may be obtained by reduction of the corresponding nitro compounds, for example using a metal such as iron or zinc, in a protic or acidic solvent such as ethanol or acetic acid, or alternatively with tin derivatives such as stannous chloride.

The compounds of formula (I) in which X and/or Y denote an alkylamino or dialkylamino group may be obtained, either by alkylation of the primary amine, for example by means of an alkyl halide in the presence of a tertiary base, or by reductive amination, for example by means of an aldehyde and alkali metal borohydride in a netural or acid protic medium.

These amino derivatives can, of course, also be obtained directly from the compounds of formulae (II) and (III) in which X denotes $NHR_5$ or $NR_6R_7$ and Y denotes $NR_{11}R_{12}$ from the outset, as specified in the reaction scheme above.

The compounds of formula (1) in which X and/or Y denote cyano can be obtained by reaction of the compounds of formula (I), in which X and/or Y denote halogen, especially iodine, with a cyanide, for example a metal cyanide such as cuprous cyanide, generally in an organic solvent such as pyridine or dimethylformamide. They can also be obtained directly from the compounds of formulae (II) and (III) in which X and/or Y denote cyano from the outset, as specified in the reaction scheme above.

The compounds of formula (I) in which X and/or Y denote carboxylate of formula $CO_2R$ can be obtained by reaction of the compounds of formula (I) in which X and/or Y denote cyano with gaseous hydrochloric acid in the corresponding alcohol of formula ROH as solvent, followed by hydrolysis. They can also be obtained directly from the compounds of formulae (II) and (III) in which X and/or Y denote carboxylate from the outset, as specified in the reaction scheme above.

The compounds of formula (I) in which X and/or Y denote carboxyl or carboxamide may be obtained by hydrolysis, preferably acid hydrolysis, of the corresponding compounds of formula (I) in which X and/or Y denote cyano. The hydrolysis can be carried out, for example, in an hydrochloric acid medium, in the heated state, alone or with an acidic organic cosolvent such as acetic acid, and at a temperature of from 60° to 120° C.

The compounds of formula (I) in which X denotes a group $CONR_3R_4$ and/or Y denotes a group $CONR_9R_{10}$ can be obtained by amidation of the corresponding acids, for example by reaction of the compounds of formula (I), in which X and/or Y denote a group of formula $CO_2H$, with carbonyldiimidazole in an inert solvent such as tetrahydrofuran, followed by aminolysis of the intermediate imidazolide obtained in situ by means of an amine of formula $R_3R_4HN$ or $R_9R_{10}NH$ respectively, in which the substituents $R_3$, $R_4$, $R_9$ and $R_{10}$ correspond to the definitions given above.

More especially, the compounds of formula (1) in which X and/or Y denote $CONH_2$ can also be prepared, either by partial hydrolysis of the corresponding nitriles, or by reaction of the same nitriles, for example with gaseous hydrochloric acid in formic acid.

The examples which follow illustrate the preparation of a few compounds according to the invention. The microanalyses and the IR and NMR spectra confirmed the structures of the products obtained.

EXAMPLE 1

N-{[2-(4-Methylphenyl)-6-trifluoromethylimidazo[1,2-a]-pyrid-3-yl)methyl}-N,3-dimethylbutanamide.

1.1.

2-(4-Methylphenyl)-6-trifluoromethylimidazo[1,2-a]pyridine.

10 g (0.0616 mole) of 2-amino-5-trifluoromethylpyridine and 17.5 g (0.0616 mole) of 1-bromo-2-(4-methylphenyl)-2-ethanone are mixed in 200 ml of n-propanol and the solution is heated to reflux. At the end of the reaction, the reaction mixture is concentrated under reduced pressure and the evaporation residue taken up with water and treated with an excess of ammonia solution until the pH is basic. The imidazopyridine is extracted with dichloromethane and purified by chromatography. 11.95 g (56%) of white solid are obtained.

M.p. 187°-188° C.

1.2
2-(4-Methylphenyl)-6-trifluoromethylimidazo[1,2-a]-pyridine-3-methanol.

13.S g (0.0463 mole) of imidazopyridine prepared according to 1.1. and 32 ml of 37% strength formaldehyde in water are dissolved in 160 ml of acetic acid. This solution is maintained at 60° C. for 3 hours and the solvent is then driven off under reduced pressure. The evaporation residue is taken up with 70 ml of water, 21 ml of caustic soda and Z60 ml of dichloromethane. The two-phase mixture is stirred for 1 hour and the insoluble material is then separated by filtration, washed with acetone and then ether and dried. 6.17 g of the expected alcohol (44%) are obtained.

M.p. 216°-218° C.

1.3.
N-{[2-(4-Methylphenyl)-6-trifluoromethylimidazo-[1,2-a]pyrid-3-yl]methyl}-3-methylbutanamide.

6.1 g (0.02 mole) of the alcohol obtained according to 1.2. and 40 ml of isovaleronitrile are introduced into a 250-ml round-bottomed flask. The suspension is heated to 100° C. and 5.7 ml of concentrated sulphuric acid are added to it dropwise. All the reagents go into solution, and a precipitate then appears. Ice is then added and the medium is diluted with water and treated with ammonia solution (until pH>S), and the amide is extracted with dichloromethane.

5.9 g (80%) of product are finally collected.
M.p. 212°-213° C.

1.4.
N-{[2-(4-Methylphenyl)-6-trifluoromethylimidazo-[1,2-a]pyrid-3-yl]methyl}-N,3-dimethylbutanamide.

1.23 g (0.0256 mole) of 50% strength sodium hydride in oil is suspended in 40 ml of tetrahydrofuran with 2 ml of dimethylformamide. There is added to this a solution of 60 ml tetrahydrofuran and 3 ml of dimethylformamide containing 5 g (0.012S mole) of amide prepared according to 1.3. and 1.6 ml of methyl iodide. The mixture is stirred until the evolution of gas has ceased, and then for a further 1 hour, and is concentrated under reduced pressure. The evaporation residue is taken up with water and the tertiary amide extracted with dichloromethane. After drying, 5 g (96%) of amide are obtained.

M.p. 196°-197° C.

EXAMPLE 2

N-{[Z-(4-Methylphenyl)-6-nitroimidazo[1,2-a]pyrid-3-yl]-methyl} -N,3-dimethylbutanamide.

2.1. 2-(4-Methylphenyl)-6-nitroimidazo[1,2-a]pyridine.

S1 g (0.38 mole) of 1-bromo-2-(4-methylphenyl)-2-ethanone and 53 g (0.3S mole) of 2-amino-5-nitropyridine are reacted in 900 ml of n-propanol. The solution is maintained under reflux, the reaction being followed by thin layer chromatography. When there is no further change, the mixture is evaporated to dryness. The residue is taken up with water and treated with ammonia solution 1 10 until the pH >8. The insoluble material is filtered off and dried, and then treated with dichloromethane. The insoluble portion is recrystallized in ethyl acetate, which yields a first crop. The mother liquors are then combined with the portion soluble in dichloromethane, the mixture is concentrated and a second crop of product is obtained. The two crops are purified separately by chromatography. 22 g (23%) of yellow solid are obtained overall.

M.p. 205°-206° C.

2.2.
2-(4-Methylphenyl)-6-nitroimidazo[1,2-a]pyridine-3-methanol.

14 g (0.056 mole) of imidazopyridine prepared according to 2.1. and 45 ml of 37% strength aqueous formaldehyde are added successively to 200 ml of acetic acid. The solution is heated to 60° C. for 4 hours. At the end of the reaction, the solvent is evaporated off under reduced pressure and the solid residue treated with 76 ml of water, 25 ml of caustic soda and 310 ml of dichloromethane. This two-phase mixture is stirred for ½ hour, then treated with an excess of ammonia solution and stirred for a further ½ hour. The insoluble material is collected by filtration and washed with water, then ethyl acetate and ether. 11.5 g (73%) of alcohol are obtained.

M.p. 236°-238° C.

2.3.
N-{[2-(4-Methylphenyl)-6-nitroimidazo11,2-a]-pyrid-3-yl]methyl}-3-methylbutanamide.

6.88 g (0.0242 mole) of alcohol prepared according to 2.2. and 40 ml of isovaleronitrile are introduced into a 100-ml round-bottomed flask, and the solution is brought to 100° C.. 6.7 ml of sulphuric acid are added dropwise to this suspension and the mixture is left with stirring until 2 phases are obtained. The upper phase is removed and the remainder of the reaction mixture treated with ice, then diluted with water and treated with concentrated ammonia solution until the pH>8. The insoluble material is filtered off and washed with dichloromethane and then with water, acetone and finally ether.

6.92 g of pure product are obtained.

2.24 g are recovered by partial evaporation of the dichloromethane. The two batches are combined and the product is recrystallized in ethyl acetate. M.p. 239°-241° C.

EXAMPLE 3

N-{[2-(4-Methylphenyl)-6-aminoimidazo11,2-a]pyrid-3-yl]-methyl}-3-methylbutanamide.

1 g (0.0026 mole) of amide prepared according to 2.3. and 2.5 g of stannous chloride are introduced into 25 ml of ethanol. The mixture is heated to 70° C. for 3 h, and then evaporated to dryness. The residue is taken up with water and 1 N ammonia solution and the product extracted with dichloromethane. The organic phase is dried over sodium sulphate, filtered and evaporated under reduced pressure. The evaporation residue is purified by column chromatography.

M.p. 245°-247° C.

EXAMPLE 4

N-{[6-Methyl-2-(4-trifluoromethylphenyl)imidazo[1,2-a]-pyrid-3-yl]methyl}-N,3-dimethylbutanamide. 4.1. 6-Methyl-2-(4-trifluoromethylphenyl)imidazo[1,2-a]pyridine.

24 g (0.077 mole) of 1-bromo-2-(4-trifluoromethylphenyl)-2-ethanone, 8.4 g (0.077 mole) of 2-amino-5-methylpyridine and 13 g of sodium bicarbonate are mixed in 210 ml of 95% strength ethanol, and this suspension is heated under reflux until the evolution of gas has ceased. The solvent is then evaporated off under reduced pressure and the evaporation residue is taken up with water and dichloromethane. The organic phase is decanted and dried over magnesium sulphate, and the solvent is removed by evaporation under reduced pressure. The residue is purified by column chromatography.

18.4 g (78%) of imidazopyridine are obtained.
M.p. 216°–217° C.

4.2.
6-Methyl-Z-(4-trifluoromethylphenyl)imidazo[1,2-a)-pyridine-3-methanol.

18 g (0.065 mole) of imidazopyridine obtained according to 4.1. and 46 ml of 37% strength formaldehyde in water are dissolved in 230 ml of acetic acid. The mixture is maintained a: 60° C. until the starting substance has disappeared (followed by thin layer chromatography), and is then concentrated under reduced pressure. The residue is taken up with 90 ml of water, 29 ml of caustic soda and 360 ml of dichloromethane, and the mixture is stirred for ¼ hour. The insoluble material is collected by filtration and washed with water, acetone and ether. 14 g (70%) of alcohol are obtained.
M.p. 225°–226° C.

4.3.
N-([6-methyl-2-(4-trifluoromethylphenyl)imidazol1,2-a]-pyrid-3-yl]methyl}-3-methylbutanamide.

7 g (0.02S mole) of alcohol obtained according to 4.2. and 40 ml of isovaleronitrile are introduced into a 250-ml round-bottomed flask. This suspension is heated to 100° C. and 6.5 ml of sulphuric acid are added to it dropwise. All the reagents go into solution, and a precipitate then appears. The medium is diluted with ice and then water, and the solution is then treated with ammonia solution until the pH>8 and finally with 200 ml of dichloro methane. The organic phase is decanted and dried over sodium sulphate.

After filtration and evaporation of the solvent, 8 g (90%) of amide are obtained.
M.p. 200°–202° C.

4.4. N-{[6-Methyl-2-(4-trifluoromethylphenyl)imidazo C. [1,2-a)-pyrid-3-yl]methyl}-N,3-dimethylbutanamide.

5 g (0.12S mole) of the secondary amide obtained according to 4.3. and 1.6 ml of methyl iodide dissolved in 63 ml of a tetrahydrofuran/dimethylformamide (95:5) mixture are added to a suspension of 1.23 g (0.0256 mole) of 50% strength sodium hydride in oil in a mixture of 40 ml of tetrahydrofuran and 2 ml of dimethylformamide. After the evolution of gas has ceased, stirring is maintained for 1 hour and 1 ml of methanol is then added. The solvent is evaporated off under reduced pressure, the evaporation residue taken up with water and the tertiary amide extracted with dichloromethane.

4.5 g (7%) of tertiary amide are obtained.
M.p. 129°–130° C.

EXAMPLE 5

Ethyl 4-{6-methyl-3-[(3-methylbutanoyl)aminomethyl]imidazo[1,2-a]pyrid-2-yl}benzoate.

5.1. Ethyl 4-(6-methylimidazo[1,-a]pyrid-2-yl)benzoate.

67 g (0.62 mole) of 2-amino-5-methylpyridine, 86 g (1.02 mole) of sodium bicarbonate and 143 g (0.527 mole) of ethyl 4-(2-bromoacetyl)benzoate are introduced into 1 l of ethanol. The mixture is brought to reflux for 3 hours and left standing for 19 hours, and the solid formed is recovered by filtration, washed copiously with water and dried. It is recrystallized in a dichloromethane/methanol mixture.
M p. 228°–230° C.

5.2 Ethyl 4-(3-hydroxymethyl-6-methylimidazo[1,2-a]pyrid-2-yl)benzoate.

31 g (0.1 mole) of the benzoate obtained according to 5.1. and 81 g (1 mole) of 37% strength formaldehyde in water are added successively to 200 ml of acetic acid. Stirring is maintained for several hours and the acetic acid is then evaporated off. The evaporation residue is taken up with water and then with an excess of ammonia solution until the pH is basic. The solid is extracted with dichloromethane and recrystallized in a dichloromethane/ether mixture.
M.p. 157°–159° C.

5.3. Ethyl 4-{6-methyl-3-[(3-methylbutanoyl)aminomethyl]-imidazo[1,2-a)pyrid-2-yl}benzoate.

20 ml of isovaleronitrile and 5 g (0.016 mole) of alcohol prepared according to 5.2. are mixed, 4 ml of concentrated sulphuric acid are then added dropwise and the reaction medium is heated to 100° C. until 2 phases are formed. The lower phase is treated with 100 g of ice, and diluted with water or treated with ammonia solution until the pH is basic. The amide is extracted with dichloromethane and purified by chromatography. A white solid is obtained.
M.p. 230°–231° C.

EXAMPLE 6

N-[({6-Methyl-2-[4-(1-piperidyl)phenyl]imidazo[1,2-a]pyrid-3-yl}methyl)-N,3-dimethylbutaamide.

6.1. 6-methyl-2-(4-nitrophenyl)imidazo[1,2-a-]pyridine.

59.5 g (0.2 mole) of 1-bromo-2-(4-nitrophenyl)-2-ethanone, 21.6 g (0.2 mole) of Z-amino-5-methylpyridine and 34 g of sodium bicarbonate are reacted in Z00 ml of 95% strength ethanol. Stirring and refluxing are maintained for 3 hours, and the reaction mixture is then cooled and the ethanol evaporated off under reduced pressure. The evaporation residue is stirred in 700 ml of water at 70° C. for 3 hours, and the insoluble material is then filtered off, washed with 50 ml of ethanol and then ether and dried.
M.p. 237°–239° C.

6.2.
6-Methyl-2-(4-nitrophenyl)imidazo[1,2-a]pyridine-3-methanol.

50 g (0.2 mole) of imidazopyridine obtained according to 6.1. and 140 ml of 37% strength aqueous formaldehyde are mixed in 700 ml of glacial acetic acid, and the solution is brought to 60° C. for 3 hours. The solvent is then evaporated off under reduced pressure and the evaporation residue taken up with water, treated with ammonia solution until the pH>8, and taken up between water and dichloro-methane. The insoluble material is separated by filtration and washed with ether. It is recrystallized in a mixture of methanol and ethanol.

36 g (64%) of product are obtained.
M.p. 237°–238° C.

6 3.
N-{[6-Methyl-2-(4-nitrophenyl)imidazo[1,2-a]pyrid--yl]methyl)-3-methylbutanamide.

0.8 ml of concentrated sulphuric acid is introduced dropwise and with stirring into 20 ml of isovaleronitrile containing 2 g (0.0076 mole) of alcohol obtained according to 6.2. The suspension is then heated until two phases are formed. The supernatant liquid is removed and the remainder of the liquid hydrolysed and then treated with an excess of ammonia solution until the pH>8. The insoluble material is extracted with dichloromethane; after drying, filtration and evaporation of the solvent, 9.10 g (88%) of secondary amide are obtained.

M.p. 221°–222° C.

6.4
N-{[6-Methyl-2-(4-nitrophenyl)imidazo[1,2-a]pyrid-yl]methyl}-N,3-dimethylbutanamide.

A solution of 85 ml of tetrahydrofuran/dimethylformamide (95:5) containing 7 g (0.019 mole) of amide obtained according to 6.3. and 2.4 ml of methyl iodide is added to a suspension of 1.83 g (0.076 mole) of sodium hydride (at 50% strength in oil) in 50 ml of a tetrahydrofuran/dimethylformamide (95:5) mixture. The suspension is maintained with stirring until 1 hour after the evolution of gas has ceased. The excess sodium hydride is destroyed with methanol and the solvents are then evaporated off under reduced pressure. The solid residue is taken up with water and dichloromethane. The organic phase is decanted, dried over sodium sulphate and filtered, and the solvent evaporated off. The solid obtained is purified on a chromatography column and then by recrystallization in a mixture of ethyl acetate and cyclohexane.

4.7 g (65%) of product are obtained.
M.p. 157°–159° C.

6.5.
N-([6-Methyl-2-(4-aminophenyl)imidazo[1,2-a]pyrid-3-yl]methyl}-N,3-dimethylbutanamide.

3.5 g (0.0144 mole) of amide obtained according to 6.4., 3.42 g of powdered iron and 6 g of acetic acid are reacted in 100 ml of absolute ethanol. The suspension is heated under reflux for 4 hours 30 min and then cooled. The ethanol and the acetic acid are driven off under reduced pressure, the residue is treated with 350 ml of water and the product is extracted with dichloromethane. After purification by chromatography, 4.4 g (87%) of product are obtained.

M.p. 178°–179° C.

6.6.
N-[{6-Methyl-2-[4-(1-piperidyl)phenyl]imidazo[1,2-a]-pyrid-3-yl}methyl]-N,3-dimethylbutanamide.

1.7 g (0.00485 mole) of amide obtained according to 6.5., 120 ml of dry toluene, 0.56 g (0.00243 mole) of 1,5-dibromopentane and 0.75 g (0.0058 mole) of ethyl-diisopropylamine are introduced successively into a 250-ml round-bottomed flask. The mixture is heated under reflux for 13 hours and then concentrated under reduced pressure. The oily residue is purified directly by chromatography.

A yellowish oil is obtained, the hydrochloride of which is prepared in a mixture of isopropyl alcohol and M.p. 116°–118° C.

EXAMPLE 7
N-{[6-Methyl-Z-(4-diethylaminophenyl)imidazo[1,2-a]pyrid-3-yl]methyl}-N,3-dimethylbutanamide.

1.3 g (0.0037 mole) of amide obtained according to 6.5. is dissolved in 25 ml of methanol containing 0.6 g (0.0013 mole) of acetaldehyde in a round-bottomed flask maintained under argon. A solution of 0.5 g (0.0079 mole) of sodium cyanoborohydride and 0.55 g (0.0039 mole) of zinc chloride in 8 ml of methanol is added to this mixture.

After 1 hour's reaction, 0.5 ml of acetic acid is added and stirring is maintained for a further 2 hours at room temperature, and then overnight at 50° C. The reaction mixture is then treated with 20 ml of 0.1 N sodium hydroxide and the solvents are driven off under reduced pressure. The evaporation residue is treated with dichloromethane, and the organic phase is washed with water, decanted and dried.

After evaporation of the solvent, the product obtained is purified by chromatography.

An oil is obtained, the dihydrochloride of which is prepared in a mixture of isopropyl alcohol and ether.
M.p. 158°–160° C.

EXAMPLE 8
N-{([6-Dimethylamino-2-(4-methylphenyl)imidazo[1,2-a]pyrid-3-yl]methyl}-N,3-dimethylbutanamide.

8.1.
N-{[6-Dimethylamino-Z-(4-methylphenyl)imidazo[1,2-a]-pyrid-3-yl]methyl}-3-methylbutanamide.

8 ml (0.0025 mole) of 3M sulphuric acid and 6 ml (0.072 mole) of formaldehyde in 40% strength aqueous solution are introduced into 83 ml of tetrahydrofuran. 4 g (0.0118 mole) of amine prepared according to 3 are added to this solution, and the mixture is left stirred for 20 min. It is cooled in a bath of ice-cold water and 3.12 g (0.0826 mole) of sodium borohydride are then added in small portions.

The pH of the solution should remain in the region of 4; if required, 3M sulphuric acid is added. At the end of the reaction, the mixture is treated with potassium carbonate in aqueous solution and the product is extracted with dichloromethane. The organic phase is washed and dried and the solvent is evaporated off. The evaporation residue is purified by column chromatography and then taken up with ether. 2.3 g (53%) of solid are obtained.

M.p. 173°–175° C.

8.2.
N-{(6-Dimethylamino-2-(4-methylophenyl)imidazo[1,2-a]-pyrid-3-yl]methyl)-N,3-dimethylbutanamide.

2 g (0.0054 mole) of amide prepared according to 8.1. and 1.56 g (0.0109 mole) of methyl iodide dissolved in a mixture of 25 ml of tetrahydrofuran and 2.5 ml of dimethylformamide are added to a suspension of 0.526 g (0.0109 mole) of 50% strength sodium hydride in oil in a mixture of 20 ml of tetrahydrofuran and 2 ml of dimethylformamide. After the evolution of gas has ceased, stirring is maintained for 1 hour and 1 ml of methanol is then added to destroy the excess sodium hydride. The solvent is evaporated off under reduced pressure, the evaporation residue taken up with water and the tertiary amide extracted with dichloromethane. The product is purified by flash column chromatography, and its hydrochloride is then prepared and recrystallized in methyl ethyl ketone. 0.6 g (27%) of salt is thereby obtained.

M.p. 200°–202° C.

EXAMPLE 9

3-{[Methyl-(3-methylbutanoyl)amino]methyl)-2-(4-methylphenyl) imidazo[1,2-a]pyridine-6-carbonitrile.

3.7 g (0.041 mole) of cuprous cyanide and 19 g (0.041 mole) of n-{[6-iodo-2-(4-methylphenyl)imidazo-[1,2-a]pyrid-3-yl]methyl}-N,3-dimethylbutanamide, prepared according to the process described in European Patent Application No. 0,172,096, are introduced into 100 ml of dimethylformamide. The mixture is heated under reflux for 4 hours and the solvent then evaporated off under reduced pressure. The residue is taken up with water and dichloromethane and the mixture treated with ammonia solution. The organic phase is washed with water and dried, and the solvent evaporated off. The residue is purified by column chromatography and taken up with pentane. 14.4 g (96%) of white solid are obtained.

M.p. 151°–153° C.

EXAMPLE 10

3-{[Methyl-(3-methylbutanoyl)amino]methyl}-2-(4-methyl-phenyl)imidazo[1,2-a]pyridine-6-carboxamide.

3.6 g (0.01 mole) of nitrile prepared according to 9 are introduced into 36 ml of formic acid, and a stream of dry gaseous hydrochloric acid is then passed through the mixture at room temperature until conversion of the nitrile is complete. When the reaction is finished, the solution is poured into 200 ml of water, ammonia solution is added and the amide is extracted with dichloromethane. It is recrystallized in methyl ethyl ketone. 2.4 g (64%) of amide are obtained.

M.p. 231°–233° C.

EXAMPLE 11

Ethyl 3-{[methyl-(3-methylbutanoyl)amino]methyl}-2-(4-methylphenyl)imidazo[1,2-a]pyridine-6-carboxylate.

3.6 g (0.01 mole) of nitrile prepared according to 9 are introduced into 36 ml of dry ethanol, and this flask flushed with argon. The solution is stirred for 1 hour at 40° C., and then cooled and saturated with a stream of dry gaseous methylamine. Stirring is maintained overnight and the solvent then evaporated off. The evaporation residue is taken up with water and dichloromethane, the organic phase is separated, washed with water and dried, and the solvent is evaporated off. The evaporation residue is purified by chromatography. 0.94 g (57%) of amide is obtained.

M.p. 158°–160° C.

EXAMPLE 14

N,N-Dimethyl-3-{[methyl-(3-methylbutanoyl)amino]methyl}-2-(4-methylphenyl)imidazo[1,2-a]pyridine-6-carboxamide.

1.6 g (0.0042 mole) of acid prepared according to 2, 0.S2 g (0.005 mole) of carbonyldiimidazole and 20 ml of dry tetrahydrofuran are introduced into a round-bottomed flask flushed with argon. The suspension is heated to 40° C. for 2 h, and then cooled and saturated with a stream of gaseous dimethylamine. At the end of the reaction, the solution is evaporated under reduced pressure and the residue taken up with water and dichloromethane. The organic phase is separated and dried and the solvent evaporated off. The residue is purified by column chromatography. 0.94 g (52%) of amide is obtained.

M.p. 134°–136° C.

EXAMPLE 15

4-{6-methyl-3-[(3-methylbutanoyl)aminomethyl]imidazo[1,2-a]-pyrid -2-yl}benzonitrile.

15.1. 4-(6-Methylimidazo[1,2-a]pyrid-2-yl)benzonitrile.

70 g (0.647 mole) of 5-methyl-2-pyridamine, 145 g (0.647 mole) of 4-(2-bromoacetyl)benzonitrile and 110 g (1.294 mole) of sodium bicarbonate are introduced into 1.2 l of 95% strength ethanol. The suspension is heated under reflux for 2 h and then filtered and evaporated to dryness. The residue is taken up with water and treated with dichloromethane. The organic phase is separated and dried, and the solvent evaporated off. The residue is taken up with ether. 107 g (71%) of imidazopyridine are obtained.

M.p. 228°–230° C.

15.2. 4-[6-Methyl-3-(hydroxymethyl)imidazo[1,2-a]pyrid-2-yl)benzonitrile.

70 g (0.3 mole) of imidazopyridine prepared according to 17.1., 1.5 l of acetic acid and 210 ml of formaldehyde in 37% strength solution in water are introduced into a 2-l three-necked round-bottomed flask. The mixture is stirred for 3 h at 50° C. and the acetic acid and water are then evaporated off. The residue is taken up with water and dichloromethane and then treated with an excess of ammonia solution, and the alcohol precipitates. It is filtered off, washed with acetone and dried under vacuum. 52 g (66%) of alcohol are obtained.

15.3. 4-{6-Methyl-3-[(3-methylbutanoyl)aminomethyl]-imidazo [1,2-a]pyrid-2-yl}benzonitrile.

500 ml of isovaleronitrile and 50 g (0.189 mole) of alcohol prepared according to 15.2. are introduced into a 250-ml round-bottomed flask, and 57 ml of concentrated sulphuric acid are added rapidly to this mixture. The suspension is heated until two liquid phases are obtained. The two-phase mixture is hydrolysed with ice and then treated with an excess of ammonia solution. The precipitate formed is filtered off, washed with water and dried under vacuum. It is purified by column chromatography. 24 g (37%) of product are obtained.

M.p. 231°-233° C.

The table which follows illustrates the structures and physical properties of some compounds according to the invention.

Antagonism towards chronic convulsions induced by Cardiazol (Trade Mark) in mice.

A trial which was modeled on the procedure described by Goodman et al., J. Pharm. Exp. Ther., (1953), 108, 168–176 was carried out on mice. Mice received the test products, or, as a control, the solvent alone, intraperitoneally 30 minutes before the intravenous injection of 35 mg/kg of Cardiazol. The animals were then observed for one hour and, for each batch, the percentage of mice showing clonic convulsions was noted (100% of clonic convulsions and 10 to 20% of tonic convulsions in the control animals).

TABLE (I)

| Compound | Y | X | $R_1$ | $R_2$ | m.p. (°C.) |
|---|---|---|---|---|---|
| 1 (Ex. 1.3) | $CF_3$ | $CH_3$ | H | $iC_4H_9$ | 212–213 |
| 2 (Ex. 1.4) | $CF_3$ | $CH_3$ | $CH_3$ | $iC_4H_9$ | 196–197 |
| 3 | $CF_3$ | $SCH_3$ | H | $iC_4H_9$ | 231–232 |
| 4 | $CF_3$ | $SCH_3$ | $CH_3$ | $iC_4H_9$ | 180–182 |
| 5 (Ex. 2.3) | $NO_2$ | $CH_3$ | H | $iC_4H_9$ | 239–241 |
| 6 (Ex. 3) | $NH_2$ | $CH_3$ | H | $iC_4H_9$ | 245–247 |
| 7 (Ex. 4.3) | $CH_3$ | $CF_3$ | H | $iC_4H_9$ | 200–202 |
| 8 (Ex. 4.4) | $CH_3$ | $CF_3$ | $CH_3$ | $iC_4H_9$ | 129–130 |
| 9 (Ex. 5.3) | $CH_3$ | $CO_2C_2H_5$ | H | $iC_4H_9$ | 230–231 |
| 10 (Ex. 6.6) | $CH_3$ | piperidino | $CH_3$ | $iC_4H_9$ | 116–118 |
| 11 | $CH_3$ | morpholino | $CH_3$ | $iC_4H_9$ | 137,5–138 |
| 12 (Ex. 7) | $CH_3$ | $N(C_2H_5)_2$ | $CH_3$ | $iC_4H_9$ | 158–160** |
| 13 | $CH_3$ | $NHC_2H_5$ | $CH_3$ | $iC_4H_9$ | 173–174 |
| 14 | $CH_3$ | pyrrolidino | $CH_3$ | $iC_4H_9$ | 153–154** |
| 15 | $NHCH_3$ | $CH_3$ | H | $iC_4H_9$ | 252–254 |
| 16 (Ex. 8.1) | $N(CH_3)_2$ | $CH_3$ | H | $iC_4H_9$ | 173–175 |
| 17 | $NHCH_3$ | $CH_3$ | $CH_3$ | $iC_4H_9$ | 175–177 |
| 18 (Ex. 8.2) | $N(CH_3)_2$ | $CH_3$ | $CH_3$ | $iC_4H_9$ | 200–202* |
| 19 (Ex. 9) | CN | $CH_3$ | $CH_3$ | $iC_4H_9$ | 151–153 |
| 20 (Ex. 10) | $CONH_2$ | $CH_3$ | $CH_3$ | $iC_4H_9$ | 231–233 |
| 21 (Ex. 11) | $CO_2C_2H_5$ | $CH_3$ | $CH_3$ | $iC_4H_9$ | 158–160 |
| 22 (Ex. 13) | $CONHCH_3$ | $CH_3$ | $CH_3$ | $iC_4H_9$ | 183–185 |
| 23 (Ex. 12) | $CO_2H$ | $CH_3$ | $CH_3$ | $iC_4H_9$ | 227–229 |
| 24 (Ex. 14) | $CON(CH_3)_2$ | $CH_3$ | $CH_3$ | $iC_4H_9$ | 134–136 |
| 25 (Ex. 15.3) | $CH_3$ | CN | H | $iC_4H_9$ | 231–233 |
| 26 | $CH_3$ | CN | $CH_3$ | $iC_4H_9$ | 147–147 |
| 27 | $CH_3$ | $CONH_2$ | H | $iC_4H_9$ | 271–272 |
| 28 | $CH_3$ | $CONH_2$ | $CH_3$ | $iC_4H_9$ | 225–227 |
| 29 | $CH_3$ | $CO_2C_2H_5$ | $CH_3$ | $iC_4H_9$ | 113–115 |
| 30 | $CH_3$ | $CONHCH_3$ | $CH_3$ | $iC_4H_9$ | 189–190 |
| 31 | $CH_3$ | $CON(CH_3)_2$ | $CH_3$ | $iC_4H_9$ | 116–118 |
| 32 | $CH_3$ | $CO_2H$ | $CH_3$ | $iC_4H_9$ | 240–242 |

*hydrochloride
**dihydrochloride

The compounds of the present invention were subjected to pharmacological trials to demonstrate their therapeutic acitivites.

Acute toxicity

This was determined intraperitoneally in mice. The $LD_{50}$ values are greater than 500 mg/kg.

For each dose, the percentage protection relative to the control animals was calculated, and the $AD_{50}$, the dose which protects 50% of the animals as regards the on effects of Cardiazol, was determined graphically.

The $AD_{50}$ of the compounds of the invention are from 0.1 to more than 30 mg/kg.

Action on the electrocorticogram of ventilated curarized rats.

The sedative or hypnotic activity of the compounds was determined by observing their action on the electrocorticogram of rats according to the method described 0) and by H. Depoortere and M. Decobert, J. Pharmacol. (Paris), 14, 2, 195–265 (1983).

The test compounds were administered intraperitoneally at increasing doses from 1 to 30 mg/kg.

They induced sleep traces from doses ranging from 0.01 to 30 mg/kg.

Effects on the duration of "sleep" induced by sodium 4-hydroxybutyrate.

This action was determined by the influence of a compound on the duration of "sleep" induced by sodium 4-hydroxybutyrate (GHB) in curarized rats.

The animals used were male Charles River strain rats weighing 200±20 g. The animals, curarized with alloferin in the proportion of 1 mg/kg i.p., were placed under artificial respiration using a mask applied over the muzzle (breathing rate =50/minute; respiratory volume =14 ml).

The oesophagus was ligated beforehand in order to prevent the entry of air into the stomach.

Frontoparietal and occipital cortical electrodes were used to enable the electrocorticographic activity to be recorded on a Grass 79 P (Trade Mark) polygraph at a speed of 6 mm/s. The preparation of the animal was performed under local anaesthesia (2% strength xylocaine). The rats were maintained throughout the experiment at constant temperature (37.5° C). Ten minutes after completion of the preparation of each rat, a dose of 200 mg/kg of sodium 4-hydroxybutyrate was injected intravenously in its tail.

A dose of 10 mg/kg of the test compound was administered intrperitoneally 3 minutes after the administration of the sodium 4-hydroxybutyrate.

Assessment of the traces was performed on the basis of 15-minute periods during 75 minutes after the injection of GHB. During this period of analysis, the total duration of the "sleep" was determined. A series of 15 controls enabled the duration of the "GHB sleep" to be precisely defined.

Statistical analysis of the results was carried out using the Mann-Whitney "U" test.

Some compounds reduced the effects of GHB (up to 40% decrease in the duration of the sleep at a dose of 10 mg/kg), while others boosted these effects (up to 25% increase in the duration of the sleep at a dose of 10 mg/kg). It was also found that the effects can be opposite, according to whether the compounds were administered at high or low doses.

Drinking conflict test in rats.

This test is described by Vogel J. R., Beer B. and Clody D. E. in Psychopharmacologica, 21, 1–7, (1971).

Male Wistar rats (IFFA Credo) were used. Their drinking water was withdrawn 24 hours before the test. On the day of the test, 30 minutes after intraperitoneal treatment with the compounds of the invention, each rat was placed in a transparent plastic cage (24×20×21 cm) having a meshwork floor which could be electrified. Drinking water was distributed via a pipette projecting 2 cm from one wall of the cage and placed 3 cm above the floor of the cage.

After a 10 to 90 second exploration, the rats found the pipette and started to drink. After giving 20 licks with the tongue (recorded by an Omnitech (Trade Mark) anxiometer), the rat received an electric shock of 0.07 mA applied to its tongue (delivered by the anxiometer), which stopped when the rat left the pipette. This test then continued for 3 minutes after the first shock; the animals continued to receive a shock every 20 licks until they stopped or until the end of the session.

Under these experimental conditions, the control animals accepted, on average, 3 to 6 shocks. The number of shocks obtained with the treated animals was noted, and this number was compared with that of the control animals by a Dunett test. The MED, the minimal effective dose, which is the first dose which significantly increases the number of shocks accepted by an animal relative to the control animals, was determined in this manner.

The MED values of the compounds are from 1 to 100 mg/kg intraperitoneally.

Analgesic activity

This was shown by using the test of Koster et al. (acetic acid "writhing" test in mice), Fed. Proc., 18, 412, 1959.

The test compound, dissolved in Tween 80 (Trade Mark) at a concentration of 1%, was administered orally to fasted mice in a proportion of 0.2 ml per 20 g of bodyweight; after 30 min, acetic acid (dissolved at a concentration of 0.6% in a mixture of carboxymethylcellulose and Tween 80, in a proportion of 10 ml per kg of bodyweight) was administered intraperitoneally. The total number of contortions was noted during 15 min.

The percentage protection relative to a control batch was determined, and the $AD_{50}$ was calculated graphically (dose which protects 50% of the animals).

The $AD_{50}$ of the compounds of the invention ranges from 5 to 50 mg/kg p.o.

Stress ulceration.

The technique used is that of Senay and Levine, Proc. Soc. Exp. Biol. 1967, 124, 1221–1223, Peptic Ulcers. The test was carried out on female Wistar rats weighing 180–210 g, kept fasted for 20 hours and distributed in randomized groups.

The animals were held in restraint in cylindrical boxes 20 cm×5 cm, and placed in a cold room at from 2 to 4° C.

The test compounds were administered orally in a proportion of 10, 30 and 100 mg/kg immediately before the restraints, the control rats receiving only placebo. 2 hours later, the animals were sacrificed by inhalation of chloroform.

The stomachs were removed and the degree of ulceration noted.

The compounds of the invention significantly decreased the amount of stress ulceration, at doses ranging from 0.1 to 10 mg/kg orally.

The results of these different tests show that the compounds of the invention possess at least one anxiolytic, sleep-inducing, hypnotic, anticonvulsant, analgesic or stress-ulceration inhibitory property The compounds of the invention are useful for, example, in the treatment of anxiety states, sleep disorders and other neurological and psychiatric conditions, disorders of altertness, and can be especially useful for combating behavioural disorders which can be ascribed to cerebral vascular damage and to cerebral sclerosis in geriatrics, for treating temporary loss of consciousness due to cranial trauma and for treating metabolic encephalopathies, as well as for treating pain, various aches and stress ulcers.

The compounds of the invention can be presented in any form suitable for oral or parenteral administration, for example in the form of tablets, dragees, gelatin capsules, solutions to be taken by mouth or injectable solutions in combination with any pharmaceutically suitable excipient The daily dosage can range from 0.1 to 500 mg.

We claim:

1. A compound of the formula

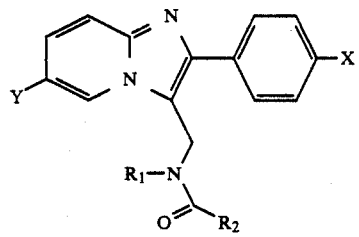

in which $R_1$ denotes hydrogen, linear or branched $C_1$–$C_4$ alkyl, or benzyl;

$R_2$ denotes linear or branched $C_1$–$C_6$ alkyl, cyclohexyl, trichloromethyl, 1-propenyl, allyl, phenyl, 4-chlorophenyl, or benzyl, or $R_1$ and $R_2$ together denote a $C_3$–$C_5$ aliphatic chain;

X denotes optionally esterified carboxy of formula -COOR in which R denotes hydrogen or $C_1$–$C_6$ alkyl; cyano; optionally mono- or dialkylated aminocarbonyl of formula —$CONR_3R_4$ in which $R_3$ and $R_4$ independently denote hydrogen or $C_1$–$C_4$ alkyl or together denote a chain of formula —$(CH_2)_2$—Z—$(CH_2)_2$— in which Z denotes a direct bond, oxygen, sulphur, or a divalent group of formula —$CH_2$—, —NH— or —N($C_1$–$C_4$alkyl)—; or a group of formula

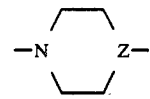

in which Z denotes a direct bond, oxygen, sulphur, or a divalent group of formula —$CH_2$—, —NH— or —N($C_1$–$C_4$-alkyl)-; and Y denotes hydrogen, halogen or methyl;

or a pharmaceutically acceptable acid addition salt.

2. A sleep-inducing, hypnotic, anxiolytic or antistress ulcer composition comprising an effective amount of a compound according to claim 1 and a pharmaceutically suitable excipient.

* * * * *